United States Patent [19]

Nye

[11] Patent Number: 4,973,707

[45] Date of Patent: Nov. 27, 1990

[54] ACETYLENE BIS-PHTHALIC COMPOUNDS AND POLYIMIDES MADE THEREFROM

[75] Inventor: Susan A. Nye, Feura Bush, N.Y.

[73] Assignee: General Electric Company, Schenectady, N.Y.

[21] Appl. No.: 386,842

[22] Filed: Jul. 31, 1989

[51] Int. Cl.$^5$ .................. C07D 709/48; C07D 307/94
[52] U.S. Cl. ...................... 548/461; 549/241
[58] Field of Search ................ 549/241, 242; 548/461, 548/473

[56] References Cited

U.S. PATENT DOCUMENTS

| | | | |
|---|---|---|---|
| 2,712,543 | 7/1955 | Gresham et al. | 549/241 |
| 3,275,651 | 9/1966 | Ellis et al. | 548/461 |
| 4,054,577 | 10/1977 | Kelles et al. | 548/461 |
| 4,609,741 | 9/1986 | Darms et al. | 549/241 |

*Primary Examiner*—Richard L. Raymond
*Assistant Examiner*—Raymond Covington
*Attorney, Agent, or Firm*—William H. Pittman; James C. Davis, Jr.

[57] ABSTRACT

Polyimides made by reacting 1,2-acetylene-4,4'-di(phthalic anhydride) with an aromatic diamine are useful in high temperature applications that require solvent resistance. Applications include components of combustion engines.

6 Claims, No Drawings

ACETYLENE BIS-PHTHALIC COMPOUNDS AND POLYIMIDES MADE THEREFROM

This invention relates to acetylene bisphthalimides and a method of making new acetylene containing polyimides therefrom.

Polyimides are useful in various applications, such as reinforcing cords in tires, and as reinforcing filaments and sheet in plastic composites. Plastic composites containing polyimides are potentially useful in high friction environments such as internal combustion engine blocks which are subjected to high temperatures and come into contact with gasoline during use and solvents during cleaning.

As is shown by Heath et al., U.S. Pat. No. 3,847,867, incorporated herein by reference, polyetherimides are valuable high performance injection moldable thermoplastic materials. Commercially available polyetherimides based upon the Heath et al. technology have good solvent resistance and a glass transition temperature of about 217° C.

As is shown by Williams et al., U.S. Pat. No. 3,983,093, incorporated herein by reference, the incorporation of a small amount of a second dianhydride such as pyromellitic dianhydride, can enhance the glass transition temperature of the polyetherimides made according to the process of Heath et al.

Related acetylene compounds include the reaction products of dianhydrides of bis(o-dicarboxyphenyloxyphenyl)acetylene and diamines as disclosed in U.S. Pat. No. 3,956,322 of Quinn et al., also incorporated herein by reference.

The present invention is based upon the unexpected discovery that polyacetyleneimides, resulting from the intercondensation of acetylene-di(phthalic anhydride) and an aryl diamine, have high glass transition temperatures, excellent solvent resistance, and improved rigidity when compared to the prior art. The same properties in other polyimides can be enhanced by the presence of units derived from 1,2-acetylene di(phthalic anhydride). Some of the second bisanhydrides and aryl diamines that can be employed in making the other polyimides are disclosed by Berdahl and Nye in U.S. Pat. No. 4,794,157, incorporated herein by reference. The Nye of the above patent is Susan Adams Nye, the same inventor as named in the present application. Aryl diamines are also referred to herein as divalent aromatic hydrocarbon-based diamines.

In its broadest sense, the composition of the present invention includes a 1,2-acetylene-bis(phthalic) compound containing one or more units having the formula

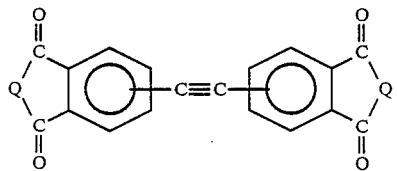

wherein: .
each Q is independently NR$^1$, —O— or

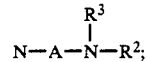

each R$^1$ is independently an aliphatic hydrocarbon-based radical containing about 1–20 carbon atoms;

each of R$^2$ and R$^3$ is independently a hydrocarbon-based radical containing about 1–20 carbon atoms, or R$^2$ and R$^3$ together form a divalent hydrocarbon-based radical containing about 4–20 carbon atoms, or R$^2$ and R$^3$ and the N to which they are attached form a polyimide or polyamic acid unit as explained below; and each A is independently a divalent hydrocarbonbased radical containing about 1–30 carbon atoms connecting the nitrogen atoms.

The term "hydrocarbon-based radical" as used herein denotes a radical having a carbon atoms directly attached to the remainder of the molecule and having predominantly hydrocarbon character within the context of this invention. Such radicals include the following:

(1) Hydrocarbon radicals, which can be aliphatic (e.g., methyl, n-propyl, isopropyl, n-butyl, 1-pentyl, 2-pentyl, 1-hexyl, oleyl or a corresponding alkylene radical), aromatic (e.g., phenyl, p-tolyl, 1-naphthyl, 2-naphthyl or corresponding arylene radical), alicyclic (e.g., cyclopentyl, cyclohexyl), aromatic or alicyclic-substituted aliphatic, aliphatic-substituted aromatic, or the like.

(2) Substituted hydrocarbon radicals; that is, radicals containing non-hydrocarbon substituents which, in the context of this invention, do not alter the predominantly hydrocarbon character of the radical. Those skilled in the art will be aware of suitable substituents (e.g., nitro, hydroxy, alkoxy, carbalkoxy).

(3) Hetero radicals; that is, radicals which while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

The R$^2$ and R$^3$ values in the compositions of this invention can be, as previously noted, aliphatic hydrocarbonbased (preferably hydrocarbon and usually alkyl) radicals containing about 1–20 and most often 1-carbon atoms, and R$^2$ and R$^3$ are then usually identical. Alternatively, R$^2$ and R$^3$ together can form a divalent aliphatic hydrocarbon-based, preferably hydrocarbon and usually alkylene radical containing about 4–20 carbon atoms such as tetramethylene, pentmethylene or alkyl-substituted derivatives thereof; in other words, R$^2$ and R$^3$ and the nitrogen atom joining them can form a heterocyclic radical such as piperidyl or pyrrolidyl.

In the polyimides (and polyamic acid precursors thereof) of the invention, R$^2$ and R$^3$, together with the nitrogen atom to which they are attached, can form a unit of the formula

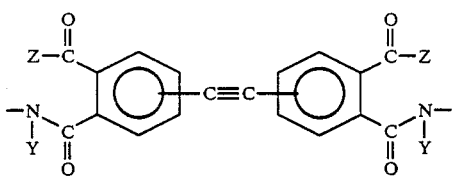

wherein Y is H and Z is OH, or Y and Z together form a single bond.

When the composition is a bis(phthalimide) the Q values are NR$^1$ and preferably each R$^1$ is independently a lower alkyl radical. The preferred phthalimide is 1,2-acetylene4,4'-bis(N-methylphthalimide). The acetylene radical can also be attached to the 3- and/or 3'-position.

The preferred polyimides of the present invention are made by the reaction of an arylene diamine with a 1,2-acetylene-di(phthalic anhydride), resulting in Q being

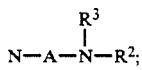

and A being as defined more particularly hereinafter. The divalent aromatic hydrocarbon-based radical contains about 6–30 carbon atoms. It can be a hydrocarbon radical or can contain other atoms such as oxygen or sulfur, so long as the other atoms do not unduly compete with amine groups in the imide-forming reaction with anhydride groups. The divalent aromatic hydrocarbon-based radical is initially contained in an aromatic diamine which is reacted with a 1,2-acetylenedi(phthalic anhydride) to produce a polyimide.

Divalent aromatic hydrocarbon-based diamines which can be used include oxydianiline; sulfonyldianiline; m-phenylenediamine; p-phenylenediamine; benzofuran diamine; diaminotetraphenylthiophene; 4,4'-diaminodiphenylpropane; 4,4'-diaminodiphenylmethane; benzidine; 4,4'-diaminodiphenyl sulfide; 4,4'-diaminodiphenyl sulfone; 4,4'-diaminodiphenyl ether; 1,5-diaminonaphthalene; 3,3'-dimethylbenzidine; 3,3'-dimethoxybenzidine; 2,4-diaminotoluene; 2,6-diaminotoluene; 2,6-diaminotoluene; 2,4-bis(β-amino-t-butyl)toluene; 1, 3-diamino-4-isopropylbenzene; m-xylylenediamine; p-xylylenediamine; 2,4-diaminotoluene and 2,6-diaminotoluene.

The polyimides comprise chemically combined units of the formula

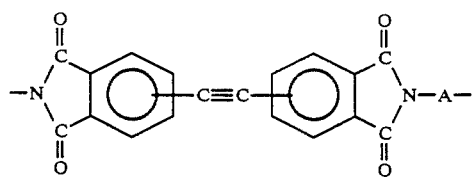

wherein each A is independently a divalent hydrocarbon-based radical containing about 1–30 carbon atoms. The divalent hydrocarbon-based radical is preferably an aromatic hydrocarbon-based radical as described above, having from 6 to about 30 carbon atoms. Each A can also independently be an alkylene radical or cycloalkylene radical having from 2-20 carbon atoms, a C$_{(2-8)}$ alkylene-terminated polydiorganosiloxane, or a divalent radical included by the formula

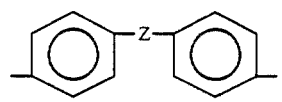

where Z is a member selected from the class consisting of

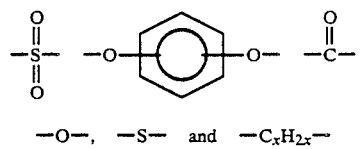

$-O-$, $-S-$ and $-C_xH_{2x}-$ and x is a whole number from 1 to 5. Such radicals and the diamines from which they are derived are described in detail in the aforementioned U.S. Pat. Nos. 4,794,157 and 3,847,867.

The method of preparing a 1,2-acetylene-bis(phthalimide) of the formula

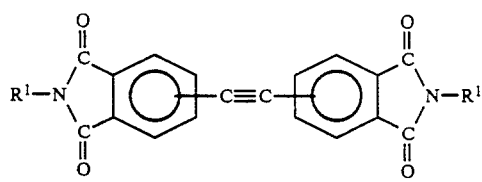

comprises
(a) reacting a halo-phthalimide having the formula

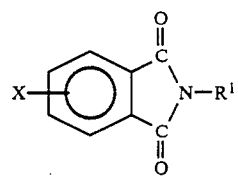

with an acetylene-phthalimide of the formula

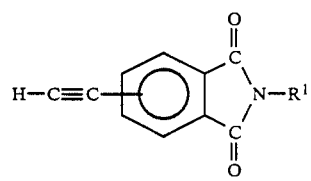

in the presence of a palladium-copper catalyst to produce the 1,2-acetylene-bis(phthalimide) of the above formula wherein X is bromide or iodide.

An alternate method involves bubbling an acetylene gas through a solution of the halo-phthalimide in the presence of the palladium-copper catalyst.

In more detail, said method comprises
(a) reacting a halo-phthalimide having the formula

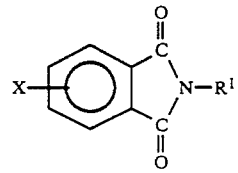

with a silylacetylene having the formula

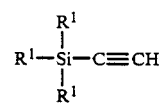

in the presence of a palladium-copper catalyst to produce a silylacetylene-phthalimide having the formula

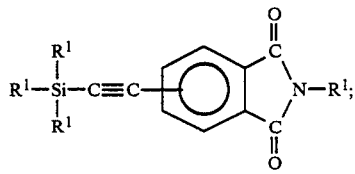

(b) removing a silyl group from said silylacetylene-phthalimide to produce an acetylene-phthalimide of the formula

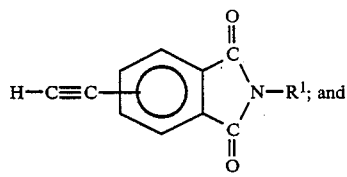

(c) reacting the acetylene-phthalimide with a halophthalimide of the above formula in the presence of a palladium-copper catalyst to produce the 1,2-acetylene-bis(phthalimide).

More specifically, the method comprises (a) reacting 4-bromo-N-methylphthalimide having the formula

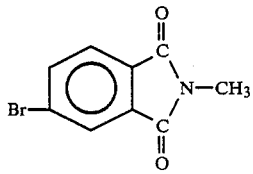

with 4-acetylene-N-methylphthalimide having the formula

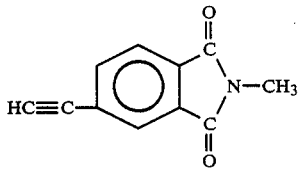

in the presence of a palladium-copper catalyst to produce a 1,2-acetylene-4,4'-bis(N-methylphthalimide) of the formula

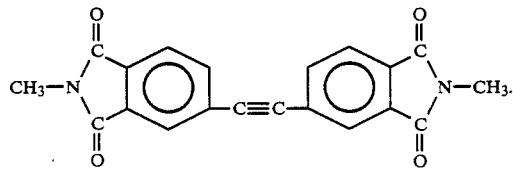

The type of palladium and copper catalyst used in the reaction between the aryl halides and aryl or vinyl acetylenes as well as the amine solvents used in such reactions are generally known in the art and described in various publications such as K. Sonagashira, Y. Tohda and N. Hagihara, *Tet. Lett.*, 4467 (1975) and E. T. Sabourin and A. Onopchenko, *J. Org. Chem.*, 48, 5135 (1983), both of which references are hereby incorporated by reference. For the reaction between a halophthalimide and an acetylenephthalimide described above, a bis(triphenylphosphine)-palladium dichloride, cuprous iodide catalyst is preferred. It is within the skill of the art to select other catalyst systems from the above publications and others for use in the present invention. Palladium acetate can also be used to replace the palladium dichloride.

The molar ratios of catalyst components and the molar ratios of catalyst to reactants are generally the same as those disclosed in the prior art. The catalyst level generally runs between 0.1 and 1.0 mole percent of palladium, based upon the level of aryl halide reactant. The copper level in the catalyst is preferably double the palladium level on a mole basis. An excess of triphenylphosphine is preferred for the reaction between the halophthalimide and the acetylenephthalimide. The trialkylsilylacetylene is preferably used in excess because it is so inexpensive. Otherwise, equimolar quantities of reactants are preferred, except in the reaction between the halo-phthalimide and acetylene gas where an excess of acetylene gas is employed.

The preferred solvents are the dialkylamines and trialkylamines which boil below 300° C. and more preferably below 250° C. The reaction tween the halophthalimide and the acetylene-phthalimide is preferably conducted at the reflux temperature of the amine solvent. The preferred solvent is triethylamine. Selection of reaction temperature is within the skill of the art and a temperature as low as room temperature can be used. Equimolar ratios of the halo-phthalimide and the acetylene-phthalimide are preferred, though other ratios are operative but wasteful.

Removal of the silyl group from the silylacetylenephthalimide may be accomplished by known methods for the breakage of silicon-carbon bonds, such as by treatment with a suitable basic reagent such as an alkali metal hydroxide, carbonate or fluoride. Fluorides are frequently preferred, with cesium fluoride often being especially preferred by reason of its relatively high solubility in organic systems.

As shown in the following examples, the 1, 2-acetylene-bis(phthalimide) produced by the reaction of the halo-phthalimide and the acetylene-phthalimide is converted to the corresponding dianhydride and reacted with a diamine to produce a polyamic acid which in turn is converted by heating to a polyimide.

The polyimides of the present invention exhibit both higher glass transition temperatures and greater solvent resistance than comparable commercial polyimides. The solubility of polyimides in certain organic solvents limits the applications for which the polymers can be used. 1,2-Acetylene-4,4'-di(phthalic anhydride) is a very linear molecule and gives rise to relatively rigid polyimides. Such polyimides can be designed to be thermally stable polyimides having a glass transition temperature greater than 250° C. and still be able to be extruded and processed at glass transition temperatures of less than 300° C. A proper combination of flexible and rigid monomers is established to provide the suitable thermal properties. Polyimides based upon 1,2-acetylene-4,4'-di(phthalic anhydride) and related monomers also provide polyimides with a site for further reaction at the triple bond.

EXAMPLES

The preparations of the 1,2-acetylene-bis(phthalimide), the 1,2-acetylene-di(phthalic anhydride) and the poly-1,2-acetylenebis(phthalimide) of this invention are illustrated by the following examples. All parts are by weight unless otherwise indicated. Monomer structures were proved correct by melting point, infrared spectra, proton magnetic spectra, ultraviolet spectra and elemental analysis.

EXAMPLE 1

Trimethylsilylacetylene (6.5 ml., 45.9 mmol.) of the formula

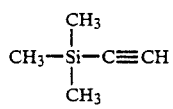

was added to a solution of 4-bromo-N-methylphthalimide (10.0 grams, 41.66 mmol.), bis(triphenylphosphine)palladium dichloride (50 mg., 0.07 mmol.), cuprous iodide (40 mg., 0.21 mmol.) and triphenylphosphine (50 mg., 0.19 mmol.) in triethylamine (100 ml.). The reaction mixture was stirred at reflux for three hours, cooled and was poured into diethyl ether (300 ml.). The triethylammonium salt was filtered and the filtrate was concentrated to a tan solid. The yield was 10.53 g. (98%). A small portion was recrystallized from hexane/ethyl acetate and proven to be 4-trimethylsilylethynyl-N-methylphthalimide of the formula

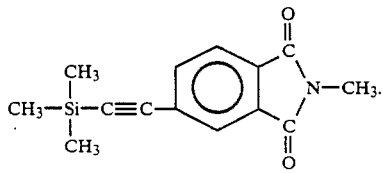

EXAMPLE 2

4-Trimethylsilylethynyl-N-methylphthalimide (10.53 grams, 40.9 mmol.) was stirred with a solution of cesium fluoride (7.0 grams, 46 mmol.) in methanol (100 ml.) at room temperature for 1-½ hours. The solution was then poured into cold water (300 ml.) and extracted with three 100 ml. portions of diethyl ether. The ethereal solution was dried with sodium sulfate, filtered and concentrated in vacuo to a light tan solid. The yield was 6.49 grams (85%). A portion of the solid was recrystallized with hot 2-propanol yielding a 54% recovery of pale tan crystals. The product was proven to be 4-ethynyl-N-methylphthalimide of the formula

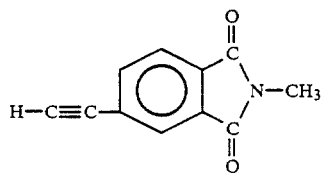

EXAMPLE 3A

4-Ethynyl-N-methylphthalimide (4.00 grams, 21.6 mmol.), 4-bromo-N-methylphthalimide (5.18 grams, 21.6 mmol.), bis(triphenylphosphine)-palladium dichloride (30 mg., 0.04 mmol.) cuprous iodide (25 mg., 0.13 mmol.) and triphenylphosphine (40 mg., 0.153 mmol.) were stirred at reflux in triethylamine (200 ml.) under nitrogen gas for 18 hours. After cooling to room temperature, the reaction mixture was poured into water. The precipitate was filtered and dried in vacuo for 18 hours for a yield of 7.00 grams (94%). The product was purified by recrystallization from hot acetic acid to yield pale yellow crystals (42% recovery). The product was proven to be 1,2-acetylene-4,4'-bis(N-methylphthalimide) of the formula

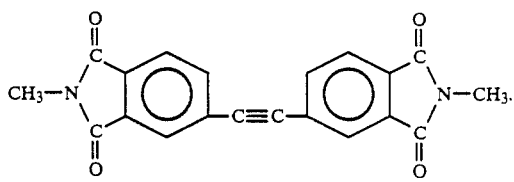

EXAMPLE 3B

This example sets forth an alternate method of making 1,2-acetylene-4,4'-bis(N-methylphthalimide). A solution containing 4-bromo-N-methylphthalimide (0.5 gram, 2.1 mmol.), bis(triphenylphosphine)palladium dichloride (7 mg., 0.01 mmol.), cuprous iodide (4 mg., 0.02 mmol.) and triphenylphosphine (4 mg., 0.015 mmol.) was stirred at reflux in triethylamine (10 ml.) under nitrogen gas. Acetylene (passed first through concentrated sulfuric acid and alumina) was bubbled through the reaction mixture for 6 hours. The contents continued to stir at reflux for 15 hours. After cooling, the contents were added to diethyl ether (50 ml.) and filtered. The ether insoluble portion was washed with water to dissolve ammonium salt and then filtered to provide a light brown solid: 0.14 gram (39% yield) of 1,2-acetylene-4,4'-bis(N-methylphthalimide).

EXAMPLE 4

1,2-Acetylene-4,4'-bis(N-methylphthalimide) (7.0 grams, 20.3 mmol.) was stirred at reflux with sodium hydroxide (9.12 grams of 50 w/w%, 114 mmol.) in water (10 ml.) for 48 hours. The reaction mixture wa then distilled to remove the methylamine/water while fresh water was added in fractions. It was then refluxed another 17 hours at which time the pH of the distillate was neutral. After cooling, it was poured into hydrochloric acid (80 ml. of 2.4 N, 192 mmol.) and the suspension stirred at room temperature for one hour. The suspension was then filtered and the solids were washed three times with 25 ml. portions of distilled water. After drying on a filter funnel, a portion of the product (0.95 grams, 2.68 mmol.) was dehydrated by refluxing with o-dichlorobenzene (50 ml.) for 8 hours while removing water with a Dean-Stark strap. After cooling the solution, a pale yellow precipitate formed that was filtered and dried in vacuo for 77 hours. The yield was 0.555 grams (65%). The product was purified by recrystallization from hot chlorobenzene (90% recovery). The product was proven to be 2-acetylene-4,4'-di(phthalic anhydride) of the formula

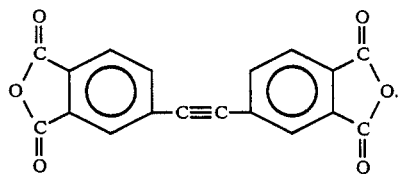

The following examples are directed to polyimides made by the reaction of 1,2-acetylene-4,4'-di(phthalic anhydride) with various aromatic diamines. Glass transition temperatures were determined using a Perkin-Elmer DSC 7 differential scanning calorimeter. Thermal gravimetric analyses were performed on a Perkin-Elmer TGA 7. Infrared spectra were made directly on the films using a Perkin-Elmer Model 598, and absorbance positions were established in reciprocal centimeters. All of the homopolymers were made in a manner similar to the procedure of the following Example 5.

EXAMPLE 5

Into a screw-capped 4 dram vial equipped with a magnetic stirbar was placed 1,2-acetylene-4,4'-di(phthalic anhydride) (0.1215 gram, 0.3817 mmol.), bis(p-aminophenyl)sulfone (0.0948 gram, 0.3817 mmol.) of the

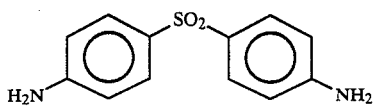

and freshly distilled dimethylacetamide (1.7 ml.). This mixture was stirred at room temperature for 5 hours at which point in time a homogeneous, viscous, clear solution of a polyamic acid was obtained. The polyamic acid contained units of the formula

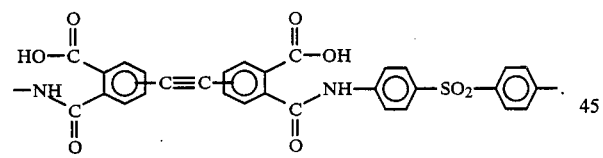

A few drops of this material were placed on several 2×3 inch glass slides and drawn into films using a 4-mil film applicator. The glass slides were placed in a programmable oven and heated as follows: Initial temperature 60° C. held for 1 minute, temperature raised 25° C./min. to 330° C. and held for 70 minutes, cooled to 30° C. over 5 minutes. The resulting polyimide films were removed from the slides by placing them in boiling water for several minutes. The resultant transparent amber-colored films were dried and analyzed. The polymer had a glass transition temperature of 344° C. It was fully soluble in hot N-methylpyrrolidinone and insoluble in hot m-cresol and dichloromethane. The solubilities of all of the following polymers and copolymers were tested in the same solvents.

EXAMPLE 6

A polyimide was made by the reaction of 1, 2-acetylene-4,4'-di(phthalic anhydride) and oxydianiline of the formula

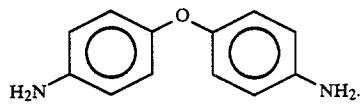

The glass transition temperature of the film was not observed, though high, the onset of decomposition was 595° C. and the polyimide was not soluble in the solvents.

EXAMPLE 7

A polyimide was made by the reaction of 1, 2-acetylene-4,4'-di(phthalic anhydride) and diaminotetraphenylthiophene of the formula

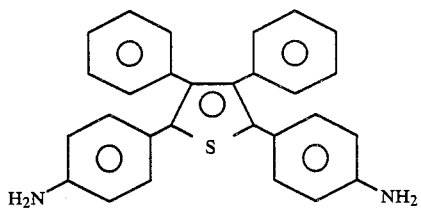

The glass transition temperature of the film was 344° C., the onset of decomposition was 584° C. and the polyimide was not soluble in the solvents.

EXAMPLE 8

A polyimide was made by the reaction of 1, 2-acetylene-4,4'-di(phthalic anhydride) and bis(anilinofluorene) of the formula

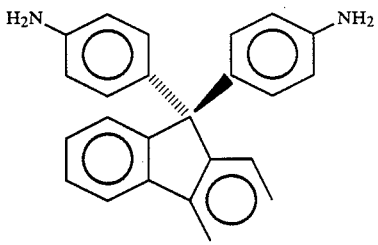

The glass transition temperature of the film was 350° C., the onset of decomposition was 588° C. and the polyimide was not soluble in the solvents, except for a slight solubility in m-cresol and a slight solubility in hot N-methylpyrrolidinone.

EXAMPLE 9

A polyimide was made by the reaction of 1, 2-acetylene-4,4'-di(phthalic anhydride) and 2-(4-aminophenyl)-5-aminobenzofuran of the formula

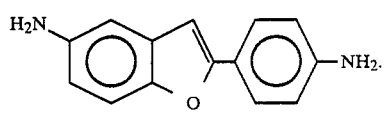

The glass transition temperature of the film was 371° C., the onset of decomposition was 611° C. and the polyimide was not soluble in the solvents.

EXAMPLE 10

A polyimide was made by the reaction of 1, 2-acetylene-4,4'-di(phthalic anhydride) and m-phenylenediamine of the formula

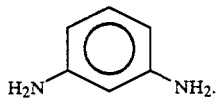

The glass transition temperature of the film was not observable, the onset of decomposition was 609° C. and the polyimide was not soluble in the solvents.

EXAMPLE 11

A number of copolyimides were made in a manner similar to the one described in this example.

Into a screw-capped 4-dram vial equipped with a magnetic stirbar was placed 1,2-acetylene-4,4'-di(phthalic anhydride) (0.1638 gram, 0.5147 mmol.), bisphenol A dianhydride (0.2679 gram, 0.5147 mmol.) of the formula

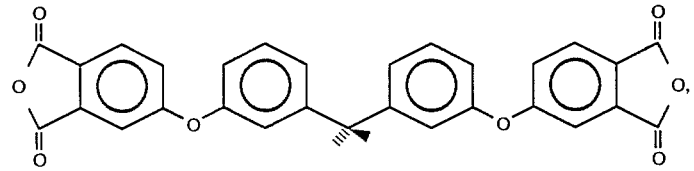

m-phenylenediamine (0.1113 gram, 1.0292 mmol.) and freshly distilled dimethylacetamide (3 ml.). This mixture was stirred at room temperature for 5 hours at which point in time a homogeneous, viscous, pale yellow solution was obtained. A few drops of this material were placed on several 2×3 inch glass slides and drawn into films using a 4-mil film applicator. The glass slides were placed in a programmable oven and heated as follows: Initial temperature 60° C. held for 1 minute, temperature raised 25° C./min. to 330° C. and held for 70 minutes, then cooled to 30° C. over 5 minutes. The polymer films were removed from the slides by placing them in boiling water several minutes. The resultant transparent amber-colored films were dried and analyzed. The resultant films had a glass transition temperature of 291° C., an onset of decomposition determined by thermal gravimetric analysis of 595° C. and were insoluble in the solvents.

EXAMPLE 12

A copolyimide as made by the reaction of 1, 2-acetylene-4,4'-di(phthalic anhydride) (20 mole %), bisphenol A dianhydride (80 mole %) and m-phenylenediamine. The glass transition temperature of the film was 250° C., the onset of decomposition was 550° C. and the polyimide was not soluble in the solvents, except for a slight solubility in hot N-methylpyrrolidinone.

For comparison purposes a polyimide prepared from bisphenol A dianhydride and m-phenylenediamine had a glass transition temperature of 217° C. and onset of decomposition was at 540° C. A similar polyimide prepared from a mixture of 20 mole percent pyromellitic dianhydride and 80 mole percent bisphenol A dianhydride had a glass transition temperature of 233° C.

What is claimed is:

1. A 1,2-acetylene-bis(phthalic) compound containing one or more units having the formula

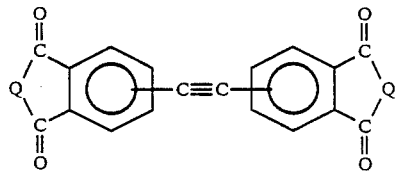

wherein:
each Q is independently NR$^1$, —O—or

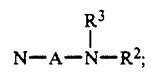

each R$^1$ is independently an aliphatic hydrocarbon-based radical containing about 1–20 carbon atoms;
each of R$^2$ and R$^3$ is independently a hydrocarbon-based radical containing about 1–20 carbon atoms, or R$^2$ and R$^3$ together form a divalent hydrocarbon-based radical containing about 4–20 carbon atoms, or R$^2$ and R$^3$ and the N to which they are attached form a unit of the formula

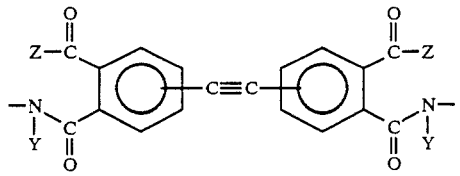

wherein Y is H and Z is OH, or Y and Z together form a single bond; and
each A is independently a divalent hydrocarbon-based radical containing about 1–30 carbon atoms connecting the nitrogen atoms.

2. A composition according to claim 1 wherein at least one Q is independently NR$^1$ and each R$^1$ is independently a lower alkyl radical.

3. A composition according to claim 2, wherein the 1,2-acetylenebis(phthalimide) is 1,2-acetylene-4,4'-bis(N-methylphthalimide 4. A composition according to claim 1 wherein at least one Q is

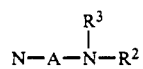

and each A is independently arylene or substituted arylene.

5. A composition according to claim 1 wherein the 1,2-acetylene-di(phthalic anhydride) is 1,2-acetylene-4,4'-di(phthalic anhydride).

6. A composition according to claim 1 wherein the 1,2-acetylene-di(phthalic anhydride) is 1,2-acetylene-3,4'-di(phthalic anhydride).

* * * * *